United States Patent
Hertz et al.

(10) Patent No.: US 6,293,856 B1
(45) Date of Patent: Sep. 25, 2001

(54) DISPOSABLE, MULTI-CONDUIT PARTICULATE MATTER PROPELLING APPARATUS

(76) Inventors: Reuben Hertz, 2318 Sea Island Dr., Fort Lauderdale, FL (US) 33301; Allen D. Hertz, 12784 Tulipwood Cir., Boca Raton, FL (US) 33428

( * ) Notice: Subject to any disclaimer, the term of this patent is extended or adjusted under 35 U.S.C. 154(b) by 0 days.

(21) Appl. No.: 09/812,644

(22) Filed: Mar. 20, 2001

(51) Int. Cl.[7] .................................................. B24C 3/00
(52) U.S. Cl. ............................................. 451/90; 451/99
(58) Field of Search .............................. 451/90, 99, 101, 451/102, 38, 39; 433/88

(56) References Cited

U.S. PATENT DOCUMENTS

| | | |
|---|---|---|
| 2,133,149 | 10/1938 | Poncelet . |
| 2,441,441 | 5/1948 | Paasche . |
| 2,577,465 | 12/1951 | Jones et al. . |
| 2,641,087 | 6/1953 | Greiser . |
| 2,696,669 | 12/1954 | Ikse . |
| 2,725,684 | 12/1955 | Crowe . |
| 2,744,361 | 5/1956 | Larson et al. . |
| 3,164,153 | 1/1965 | Zorzi . |
| 3,631,631 | 1/1972 | Greenstein . |
| 4,369,607 | 1/1983 | Bruggeman et al. . |
| 4,475,370 | 10/1984 | Starke et al. . |
| 4,941,298 | 7/1990 | Fernwood et al. . |
| 5,123,206 | 6/1992 | Woodson . |
| 5,839,946 | 11/1998 | Hertz . |
| 6,004,191 | 12/1999 | Schur et al. . |
| 6,099,306 | * 8/2000 | Lawler .................................. 433/88 |

OTHER PUBLICATIONS

Whip Mix Corp., Product "Vapor Jet" Advertisement.
Satelec Corp., Product "Air Max" Brochure.
Satelec Corp., Product "Prophy Max" Brochure.
Parkell Corp., Product "Eraser Air Polishing Prophy Pencil" Advertisement.
Sullivan/Schein Dental Corp., Product "Minipolisher" Article.
Deldent Corp., Product "Jet Polisher" Advertisement & Brochure.
Mant USA, Inc., Product "HTS Polishing System" Advertisement.
Dentsply Preventative Care, Product "Cavitron Products" Brochure.
Dentsply Preventative Care, Product "SPS Scaler & Jet" Brochure.
Dentsply Preventative Care, Product "Jet Shield" Brochure.

* cited by examiner

*Primary Examiner*—Timothy V. Eley
*Assistant Examiner*—Dung Van Nguyen (57) ABSTRACT

A disposable apparatus for propelling particulate matter against a surface of a target material includes, a mixing chamber having a chamber wall, a multi-conduit receiving port, a propellant-gas receiving conduit, a discharge conduit, and a flow through conduit. The gas delivery conduit extends from the propellant-gas receiving port into the chamber, a mixture discharge conduit extending from the mixture discharge port into the chamber, and a quantity of particulate matter inside the chamber. The flow through conduit(s) provide a means for transferring flow from the multi-conduit receiving port through the discharge wall to exit proximate the exit of the discharge port. A method is provided for propelling particulate matter against a surface of a target material using the above-described apparatus, including the steps of delivering a stream of gas into the air delivery conduit and into the mixing chamber from the gas source, so that the gas stream blows through the quantity of particulate matter, causing the particulate matter to mix with the gas stream, forming a gas and particle mixture, and discharging the mixture through the discharge conduit and the discharge port to strike the surface of the target material. The method further provides a means for transferring a second (or more) flow through the apparatus. The multiple flows can be externally mixed to increase the versatility of the apparatus. The end of the discharge conduit(s) can be designed to modify the discharge flow of the medium.

24 Claims, 6 Drawing Sheets

DISPOSABLE, MULTI-CONDUIT PARTICULATE MATTER PROPELLING APPARATUS

FIELD OF THE INVENTION

The present invention relates generally to the field of devices for propelling particulate matter, air, and fluid against a surface of target material to rinse, wash, sand-blast, abrade, etch, erase, cut, smooth, clean, polish and harden the surface. More specifically, the present invention relates to a totally disposable, inexpensive particle propelling apparatus serviced by a multi-conduit fluid supply system. The multi-conduit fluid supply system is known and commonly available in dental offices and laboratories. One such multi-flow system provides high-pressure water flow, high-pressure air, low-pressure air, and exhaust. The apparatus provides a means for mixing particulate matter with compressed air; the compressed air enters through a gas delivery port, mixes within the primary chamber, and discharges through a mixture discharge port and directed at the desired object via a particle directing hollow tube. The apparatus further provides a means for incorporating at least one of the additional services provided by the multi-flow system, such as including a water discharge port, an air-flow port, and the like. Further, the design can allow for external mixing of two or more of the additional services such as externally mixing water with the particulate matter.

The apparatus is preferably made of inexpensive plastic and metal, so that the entire unit and contents are cleanly manufactured and sealed and, if necessary, can be sterilized at the place of manufacture, and the entire apparatus is economically replaced rather than re-used.

DESCRIPTION OF THE PRIOR ART

There have long been devices and methods for impacting surfaces of a target material with specific particulate matter. This may be done for a variety of reasons, such as to remove foreign material, clean, roughen or etch the surface to enhance bonding quality, to dull an unsightly shine or and removing material such as drilling into a patient's tooth. As the gas and particulate matter bombard the target material at high speed. The impact of the particles causes layers of the target material to remove each layer, one at a time. This process of material removal is known as etching, drilling and sand-blasting. Devices of many sizes and types are available for this process, and they are powered by many types of compressed gases such as air, nitrogen, oxygen, and others. Large devices have been provided for cutting through, drilling, or any other operations to metals and smoothing surfaces of casting parts, while small ones have been designed for the art industry and dentistry. All of these devices operate on the physical property that gas at higher pressure flows and accelerates toward and into gas at lower pressure. When particulate matter is mixed with gas at higher pressure, it is accelerated with the gas. This technique utilizes kinetic energy (Ek) from particles entrained in a high-velocity stream of gas to remove material structure. The term kinetic energy was coined by Lord Kelvin and is defined mathematically by the equation Ek equals one half the mass times the square of the velocity.

While many devices operating on this principle have been designed specifically for the art industry, construction, general industry, dental, and veterinary services, the Applicant has been awarded U.S. Pat. No. 5,839,946, issued on Nov. 24, 1998 as a known disposable particle matter propelling apparatus. Hertz discloses a particulate matter-propelling device; the device mixes a gas stream with particulate matter disposed within a mixing chamber and is projected towards an object through a discharge conduit and respective port.

The other devices are designed are non-disposable for long-term use and repeated cleaning and maintenance cycles. For example, the devices are designed to be refilled with particulate matter and to operate at high pressures. These functional characteristics require that existing devices have larger overall sizes and bulky nozzles made of expensive carbide alloys. Since these devices are not disposable, individuals must be skilled to maintain, clean, sterilize, refill and re-assemble them. This presents an opportunity for unit malfunction, for contamination of the material and apparatus, and for loading with inappropriate and even dangerous particulate material by mistake.

Examples of these prior devices include that described in Fernwood, U.S. Pat. No. 4,941,298, issued on Jul. 17, 1990. Femwood discloses a rear reservoir micro sandblaster which includes a hollow tubular handle with a nozzle at one end for dispensing a mixture of a solid material and a gaseous medium and a compressed air and solid particulate material receiving member at the other end of the handle. The nozzle section of the apparatus contains a mixing chamber where a vacuum is created by the flowing pressurized gaseous medium, drawing solid material into the chamber from a rear reservoir. Problems with Fernwood are that it is too costly to be disposable; it draws particulate matter from a container using a vacuum rather than by more efficient blow through mixing of as per our invention, and is thus sensitive to variations in material and gas moisture levels, and requires an unclogging mechanism. Fernwood operates at relatively high pressures, 80–100 psi, requiring a special tap into the air-lines and limiting the range of operational pressures. In addition, Fernwood requires special training to set up and use, cannot be cost effectively and completely sterilized between uses, cannot deliver varying sizes of particles, and is contaminated after every use.

The apparatus disclosed in the Microetcher™ brochure is either the same or very similar to that of Fernwood. Another similar device, with a forward material reservoir, is disclosed in the Mirage/Chameleon Dental Products, Inc. brochure and is called the Handiblaster™. Other similar devices are the Microetcher II™ disclosed in brochure headed: "Now With Autoclavable Tip" and the AEC Air Eraser™ revealed in Paasche™ operating instructions.

The delivery of the particulate matter using a stream of gas requires that the particulate matter be dry. Surface tension of moisture can bond multiple particles into a larger particle making the apparatus inoperable. Each of the prior art is limited wherein the application is specific to propelling dry particulate matter.

Multi-conduit compressed systems are currently utilized within the medical and dental industries. One such multi-conduit compressed system provides several medium transfer paths for providing flow paths for low-pressure compressed air, high-pressure compressed air, vacuum, and fluid flow. It could be recognized that the conduits may provide a means for transferring any gas source or flow-able medium.

The multi-conduit flow source systems are designed with various interconnecting means and various means to segregate each of the different flow paths.

Thus what is desired is a low-cost, disposable, multi-port apparatus for propelling particulate matter using compressed air from a single or multi-conduit compressed source, whereby the apparatus utilizes compressed air to propel particulate matter and additionally can transfer other flowing media through the apparatus and optionally mix the media externally while projected towards a object, target, and the like.

SUMMARY OF THE INVENTION

The present invention accomplishes the following objectives, as well as others, as may be determined by a fair reading and interpretation of the entire specification.

A first objective of the present invention is to provide a sandblasting type apparatus that delivers a mixture gas and particulate matter against a surface of target material.

A second objective of the present invention is to provide an apparatus from the manufacturer that is pre-loaded with a predetermined quantity of desired particulate matter and which is sealed.

A third objective of the present invention is to provide such an apparatus which accelerates and directs particulate matter through the barrel of a hollow tube, which can be bent to become omni-directional, which is long enough to deliver the matter at a substantially uniform velocity, and which is narrow enough to focus discharged matter over a small target in a confined area.

A fourth objective of the present invention is to provide such an apparatus which allows the user to visually determine the quantity of particulate matter disposed within the apparatus.

A fifth objective of the present invention to provide such an apparatus which has an external diameter narrow enough to be handled in the manner of a writing instrument such as an airbrush or pen, preferably balanced and operational at all orientations and external pressures, and is totally sterilizable and disposable.

A sixth objective of the present invention to provide such an apparatus and method which creates a turbulent mixture of gas and particulate matter via blow through mixing of the gas stream on the particulate matter.

A seventh objective of the present invention is to provide a means for independently transferring flow of multiple mediums from the multi-conduit source coupler to the propelling particulate matter apparatus.

An eighth objective of the present invention is the ability to easily couple to a multi-conduit supply system.

A ninth objective of the present invention is a means to means to segregate each of the different flow paths.

A tenth objective of the present invention is the ability to provide a transfer path into the mixing chamber within the apparatus for at least one of the mediums and at least one transfer path through the apparatus for at least a second of the mediums.

An eleventh objective of the present invention is the ability to externally mix any of the multiple mediums.

A twelfth objective of the present invention to provide such an apparatus which is sufficiently inexpensive to manufacture to be disposable and to manufacture cleanly so that contamination is not compromised during filling, and which is recyclable.

A thirteenth objective of the present invention is to provide a means for mixing multiple mediums disposed within the mixing chamber of the propelling particulate matter device.

A fourteenth objective of the present invention is to provide an optional, removable rear seal.

A fifteenth objective of the present invention is to provide a means for determining the remaining volume of particulate matter within the apparatus.

A sixteenth objective of the present invention is a means to determine the specific type of particulate matter disposed within the specific apparatus.

A seventeenth objective of the present invention is the ability to bend any of the various discharge conduits to vary the direction of outward flow.

An eighteenth objective of the present invention is the ability to provide different discharge opening shape such to modify the flow of the discharge.

A nineteenth objective of the present invention is the ability to manufacture the apparatus of a material such to provide the ability to bulk sterilize the apparatus without damage to the apparatus. One such example is the use of molded plastic and gamma radiation.

A disposable apparatus powered by compressed gas is provided for propelling particulate matter against a surface of a target material, including a mixing chamber having a chamber wall and a gas receiving port in the chamber wall in fluid communication with a compressed gas source and having a mixture discharge port in the chamber wall, a gas delivery conduit extending from the gas receiving port into the chamber, a mixture discharge conduit extending from the mixture discharge port into the chamber, and a quantity of particulate matter inside the chamber, where a stream of gas having a pressure is delivered into the gas delivery conduit and into the mixing chamber from the gas source, the velocity of the gas stream progressively blows through the quantity of particulate matter and causes the particulate matter to mix with the gas stream, forming a gas and particle mixture which enters and passes through the discharge conduit and the discharge port, and exits the apparatus to strike the surface of the target material. The mixing chamber wall preferably has a tubular, side wall portion and two opposing end wall portions. The apparatus preferably additionally includes a hollow particulate matter delivery and directing tube.

An apparatus is also provided for propelling particulate matter against a surface of a target material, including a mixing chamber having a chamber wall and a gas receiving port in the chamber wall and having a mixture discharge port in the chamber wall, a gas delivery conduit extending from the gas receiving port into the chamber, a mixture discharge conduit extending from the mixture discharge port into the chamber, and a quantity of particulate matter inside the chamber. The apparatus further provides a means for transferring any of multiple flows from a multi-source system through the apparatus as desired by the operator.

A method is provided of propelling particulate matter against a surface of a target material using the above-described apparatus, including the steps of delivering a stream of gas into the gas delivery conduit and into the mixing chamber from the gas source, so that the flow of the gas stream progressively blows through the quantity of particulate matter, causing the particulate matter to mix with the gas stream, forming a gas and particle mixture, and discharging the mixture through the discharge conduit and the discharge port to strike the surface of the target material. The method further comprising the steps of selecting any of the available flow mediums from the multi-conduit system and directing the desired flow or flows toward the desired target.

BRIEF DESCRIPTION OF THE DRAWINGS

Various other objects, advantages and features of the invention will become apparent to those skilled in the art from the following discussion taken in conjunction with the following drawings, in which:

DETAILED DESCRIPTION OF THE PRESENT INVENTION

As required, detailed embodiments of the present invention are disclosed herein; however, it is to be understood that the disclosed embodiments are merely exemplary of the invention that may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various figures are designated by the same reference numerals.

FIGS. 1–4 illustrate the apparatus and operation of the Applicant's prior art, U.S. Pat. No. 5,839,946, issued Nov. 24, 1998.

Figure 1:
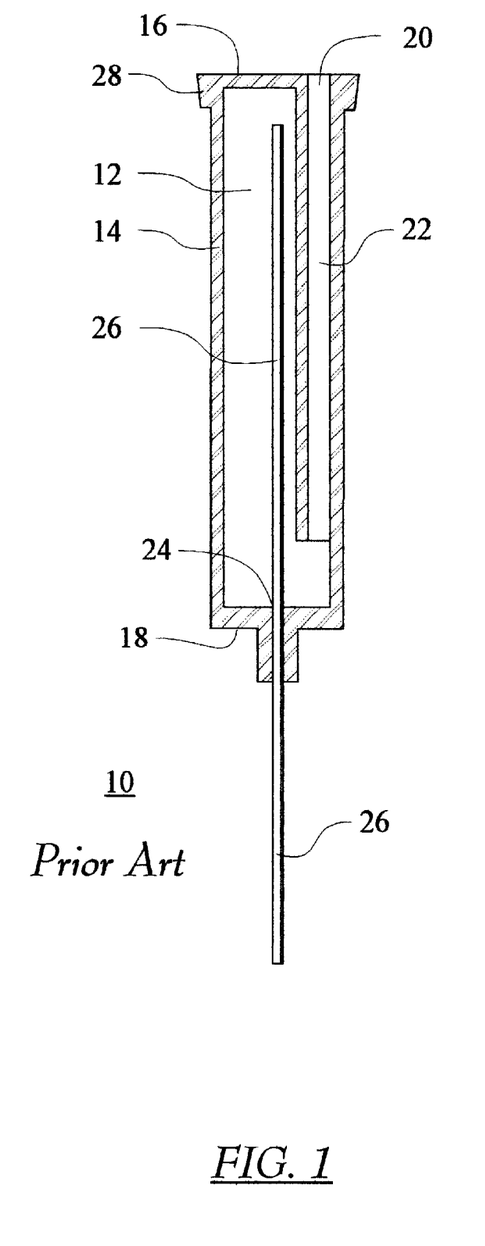
FIG. 1 is a cross-sectional side view of the prior art illustrating a single source, particle-propelling apparatus. The particulate matter, gas source, and end caps are omitted.

FIG. 1 illustrates a cross sectional view of a single-conduit, disposable particle propelling apparatus 10 for propelling particulate matter (not shown) against target material (not shown). The apparatus 10 includes a cylindrical mixing chamber 12 having a chamber wall 14 a first, receiving end wall 16 and a second, discharge end wall 18. The single-conduit, disposable particle propelling apparatus 10 is powered by a single compressed gas source such as an air compressor or a compressed gas cylinder (not shown), which connects in fluid communication to the gas receiving port 20 of receiving end wall 16. The compressed gas source is coupled to the apparatus 10 at a coupling flange 28. A propellant-gas delivery conduit 22 extends from the gas receiving port 20 into mixing chamber 12. The discharge end wall 18 includes an opening 24 for a mixture discharge port 26. The mixture discharge conduit 26 extends, in fluid communication from the mixing chamber 12 through the discharge end wall 18 to an external position some distance beyond the discharge end wall 18.

Figure 2:
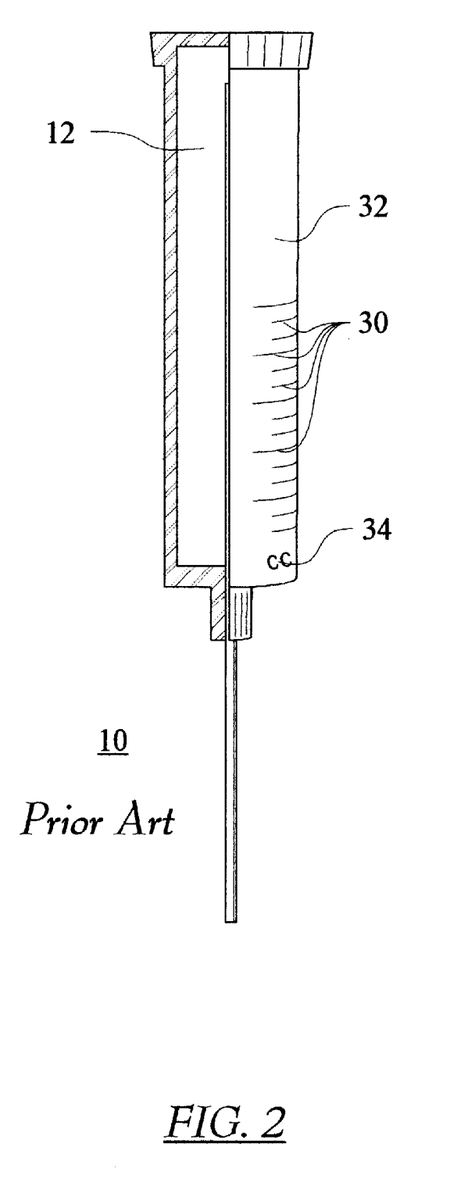
FIG. 2 is a partial cross-sectional side view of the prior art apparatus of FIG. 1, revealing a portion of the outer chamber side wall illustrating the optional grid measuring marking and a circumferential color-code band.

FIG. 2 illustrates a cut away view of the single-conduit, disposable particle propelling apparatus 10 of FIG. 1, further illustrating an optional measuring means. One optional measuring means utilizes volume grid markings 30 which can be molded into, printed upon, and the like, to the outer surface 32 of the side wall portion 14 of the mixing chamber 12. It would be preferred to include the units of measure 34. The particle size and the type of particulate matter can be identified by color coding the apparatus by manufacturing of various translucent colors, printing the volume grid markings 32 in various colors, placing a color coded tape around the body of the apparatus, and the like.

Figure 3:
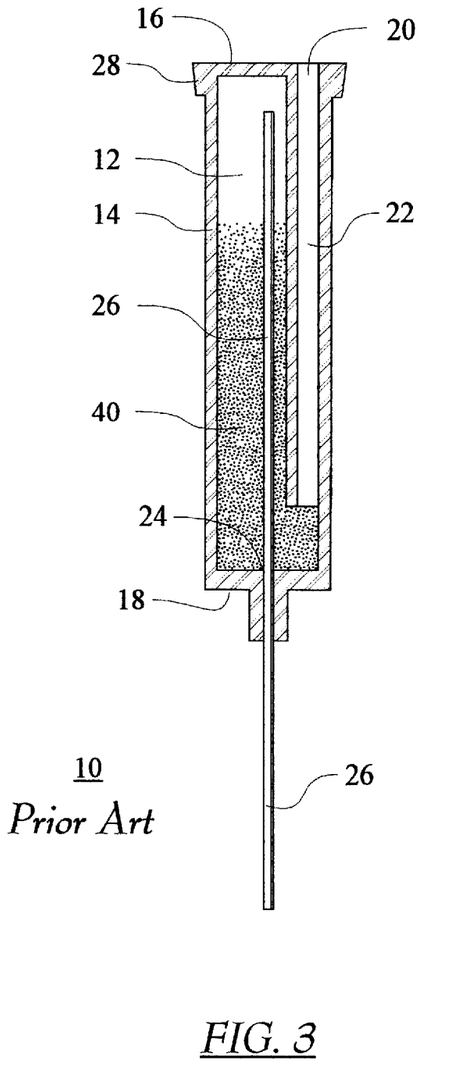
FIG. 3 is a view as in FIG. 1, showing the prior art apparatus with the particulate matter added.

FIG. 3 is a cross sectional view of the single-conduit, disposable particle propelling apparatus 10 of FIG. 1, further illustrating particulate matter 40 disposed within the mixing chamber 12 of apparatus 10. A quantity of particulate matter 40 is sealed inside mixing chamber 12, the quantity being sufficient to only partially fill said mixing chamber 12, leaving space for gas and particulate matter 40 to mix (not shown). The apparatus can be sterilized during the manufacturing process, including the particulate matter. The various openings can be sealed using seals or end caps (not shown), giving the particulate matter 40 a virtually unlimited shelf life and protection from contamination and are removed when apparatus 10 is to be readied for use.

Figure 4:
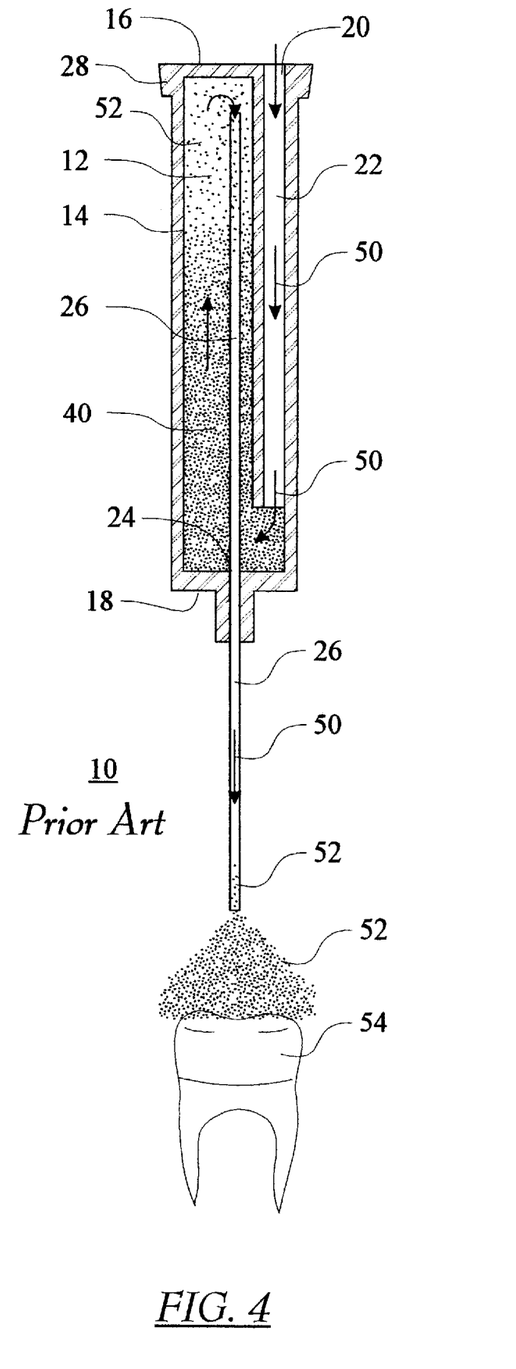
FIG. 4 is a view as in FIG. 3; with the prior art apparatus in operation, discharging the gas and particulate matter mixture toward a surface of a target material.
Figure 5:
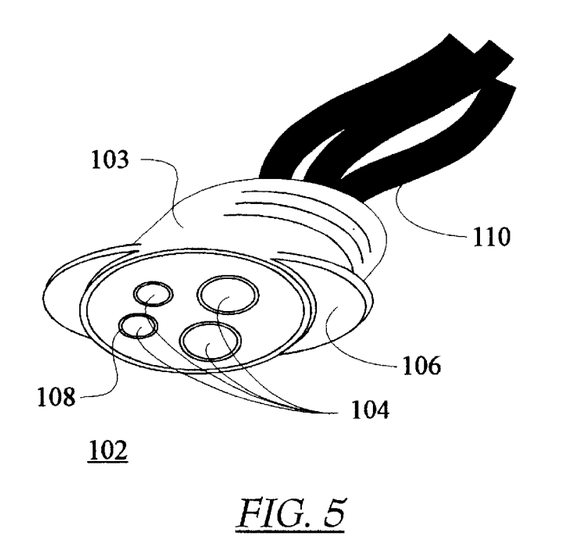
FIG. 5 is an isometric view of a multi-conduit supply source coupler.

FIG. 4 is a cross sectional view of the single-conduit, disposable particle propelling apparatus 10 of FIG. 1, further illustrating the air flow 50. The gas flow 50 would enter the single-conduit, disposable particle propelling apparatus 10 through the gas receiving port 20, flow into the mixing chamber 12 whereby the gas flow 50 fluidizes the particulate matter 40 within the mixing chamber 12, and gas flow (50) and particulate matter (40) mixture 52 is discharged through the mixture discharge conduit 26. The gas flow and particulate matter mixture 52 is directed towards an object 54 as the mixture 52 exits the discharge conduit 26. The discharge conduit 26 serves to both direct and accelerate the discharging gas and particulate matter mixture 52. As result, the particulate matter 40 can be applied to a focused region very precisely and at a uniform velocity. Since apparatus 10 is disposable, the discharge conduit 26 can be of an inexpensive, thin walled design and sustain only a limited use. The discharge conduit 26 is manually bendable permitting it to be adjusted to any angle, making the discharge omni-directional, thus providing access to-hard-to reach surfaces such as the rear teeth of a patient. The discharge conduit 26 preferably has a preset orifice diameter to accommodate a given size and type of particulate matter 40, and is preferably made of metal, but may also be formed of suitable plastic or other material.

Mixing chamber 12 is preferably an integrated chamber with balanced distribution of weight that is preferably slender enough to hold and manipulate as though it were a writing instrument. The direct, blow through, turbulent mixing within mixing chamber 12 makes apparatus 10 operational at all orientations relative to the target surface and to the direction of gravity. The slender construction makes mixing chamber 12 able to access narrow spaces and operate in small confined areas. Mixing chamber 12 can receive and function with varying gas pressures applied to gas receiving port 20, selected to accelerate particles to various desired velocities for various given tasks. Turbulent mixing of particulate matters 40 directly in the path of the gas stream within mixing chamber 12 enables apparatus 10 to deliver particulate matters 40 of a wide range of sizes, and to mix and deliver a wide range of particulate matter types. The variation in flow rate provided to the apparatus 10 can alter the performance of the apparatus 10.

Apparatus 10 contains no moving parts and is preferably made of disposable plastic, so that particulate matter 40 and apparatus 10 can be sterilized at the place of manufacture or distribution. The apparatus 10 is replaced rather than re-filled and re-used. Apparatus 10 can be of materials that withstand common sterilization techniques such as Autoclave, chemical treatments, and irradiation. Contemplated apparatus 10 construction materials may include but are not limited to plastic, stainless steel, Delrin™ and Teflon™. Apparatus 10 is lightweight, manufactured to be recyclable, and easy to use and replace without training or maintenance. Apparatus 10 can alternatively be constructed from an adapted disposable syringe of a type that is extremely common in the health care industry.

FIG. 5 illustrates a multi-conduit source connector 102 for use in conjunction with the present invention. The illustrated multi-conduit source connector 102 shows four (4) conduits 102, whereby each conduit provides a different medium to the apparatus. The multi-conduit source connector 102 comprises a body 103, two (2) or more conduits 104, and a securing means 106 to removably couple the multi-conduit source connector 102 and the multi-conduit propelling particulate matter apparatus (not shown). The preferred embodiment would couple the conduit of the multi-conduit source connector 102 and the conduits of the multi-conduit propelling particulate matter apparatus (not shown) to provide a means to transfer flow from the source to the apparatus 100. One means of accomplishing this would be to secure O-Rings 108 around the openings of the conduits to provide pneumatic seals between the two (2) devices. Each of the conduits 104 is coupled to a respective source 110, whereby the source may be a first end of a pneumatic hose whereby the second end of the pneumatic hose is coupled to a controlling valve apparatus (not shown). The controlling valve apparatus may control flow from one or more of the main supply sources. Such supply sources may include low air-pressure, high air-pressure, pressurized water, vacuum, and the like. The present invention should not be limited to the means or apparatus of controlling the flow from the multiple sources to the said multi-conduit source connector 102.

FIG. 6 illustrates a multi-conduit particle matter propelling apparatus 100. The apparatus comprises the same features as described by the prior art of FIGS. 1–4, with the addition of at least one (1) flow through conduit 120. The flow through conduit 120 includes a flow through receiving port 122, and is coupled within the multi-conduit particle matter propelling apparatus 100, preferably coupled to the receiving end wall 16 and discharging end wall 18. The flow through conduit 120 can be positioned in a manner to provide for mixing of particulate matter mixture 52 and a second medium 124. A preferred embodiment would be the ability to mix the propelled particulate matter mixture 52 and water as a second medium 124. If the water were to mix within the mixing chamber 12, the water and particulate matter may coagulate; the resulting coagulated mass would not allow the particulate matter 40 to fluidize, making the apparatus 100 inoperable. A multi-conduit foot controller (not shown) can be used as a means to control the flow of gas/fluids within the individual conduits/ports 104 of the multi-conduit source system. The flow through conduit 120 can alternatively be coupled to the chamber wall 14. It can be recognized and is illustrated herein that additional flow through conduits can be included in the multi-conduit particle matter propelling apparatus 100. The Applicants further provide that the manufacturer, user, or other can load the apparatus 100 with multiple types of particulate matter 40, whereby the multiple types of particulate matter 40 is then mixed within the mixing chamber 12 of the apparatus 100 by the cyclic action of the propelling gas.

FIG. 7 illustrates a second embodiment of the present invention, whereby the multi-conduit particle matter propelling apparatus 100 comprises two (2) receiving conduits 22 and 120. The first receiving conduit is a gas receiving conduit 22, receiving gaseous flow from a first source 110*a* of the multi-conduit connector 102. The propellant-gas delivery conduit 22 is used as a propellant for the particulate matter (40 of FIG. 6) and discharges the gaseous flow (50 of FIG. 6) into the mixing chamber 12. The second receiving conduit is a flow through conduit 120; receiving flow of a medium (gas, fluid, and the like) and discharges the flowing medium (124 of FIG. 6) external of the mixing chamber 12.

FIG. 8 illustrates the multi-conduit particle matter propelling apparatus 100 of FIG. 7, whereby the discharge conduit 26 is not placed adjacent to the flow through conduit 120. It is recognized by the Applicant's that it can be desirable to have the capability of sliding the discharge conduit 26 to change the position of the discharging end 130 of the discharge conduit 26 with respect to the position of the flow through conduit 120. The discharge end 130 of any of the conduits 26, 120 can be formed in a manner to direct the flow of the discharging medium (gas, particulate matter mixture, fluid, etc.). One such design would be an oblique opening at the discharge end 130 of the conduit 26.

FIG. 9 illustrates the multi-conduit particle matter propelling apparatus 100 of FIG. 8, the apparatus 100 further comprising a second flow through conduit 140. The propellant-gas delivery conduit 22 and flow through conduits 120, 140 are provided the source flow by the supply conduits 110*a*, 110*b*, and 110*c* of the multi-conduit connector 102.

FIG. 10 is a second design for the discharge end 130 of a conduit. The discharge end is shaped to alter the flow of fluid (not shown) as it exits the discharge conduit 26. Such alterations can include acceleration of the material, separation of the material (i.e. spray), and the like. The discharge end 130 is shaped by positioning a multiple of points 150 along the outer wall towards the center of the discharge end 130 to form reduction(s) in the cross sectional area 152 of the discharge end 130. The smaller cross sectional areas 152 accelerate the discharging flow and particulate matter (not shown). The design of the discharge end 130 can further add turbulence to the discharging flow. An alternative design for the discharge end 130 is described in FIG. 10. One means of manufacturing the discharging end 130 is of a metallic discharge conduit 26; the end of the conduit being compressed by a forming die. A second means of manufacturing the discharging end 130 is of a plastic discharge conduit 26, the end being formed during the molding process. It can be recognized that other discharge end designs may be incorporated to achieve the same desired effect.

FIG. 11 illustrates a cut-away, isometric view of a multi-conduit particulate matter propelling apparatus 100. The illustrated apparatus 100 provides for a discharge conduit 26 and a flow through conduit 120. The discharge conduit 26 and a flow through conduit 120 are shown of optional, bendable conduit material to provide the user a means for improving the direction of the propellant. The multi-conduit connector (102 of FIG. 7) would preferably couple to the coupling flange 28 of the apparatus 100. Applicant recognizes that the receiving end wall 16 can be of many designs. One such design can be of removable, rubber material. A second design can be of molded material that is adhesively coupled to the sidewall 14 of the mixing chamber 12. The discharge conduit 26 and flow through conduit 120 can be manufactured as one piece for ease of assembly and reduction of manufacturing costs. The discharge conduit 26 and flow through conduit 120 can be coupled in a manner whereby the two can move dependently of each other.

Method

Figure 6:
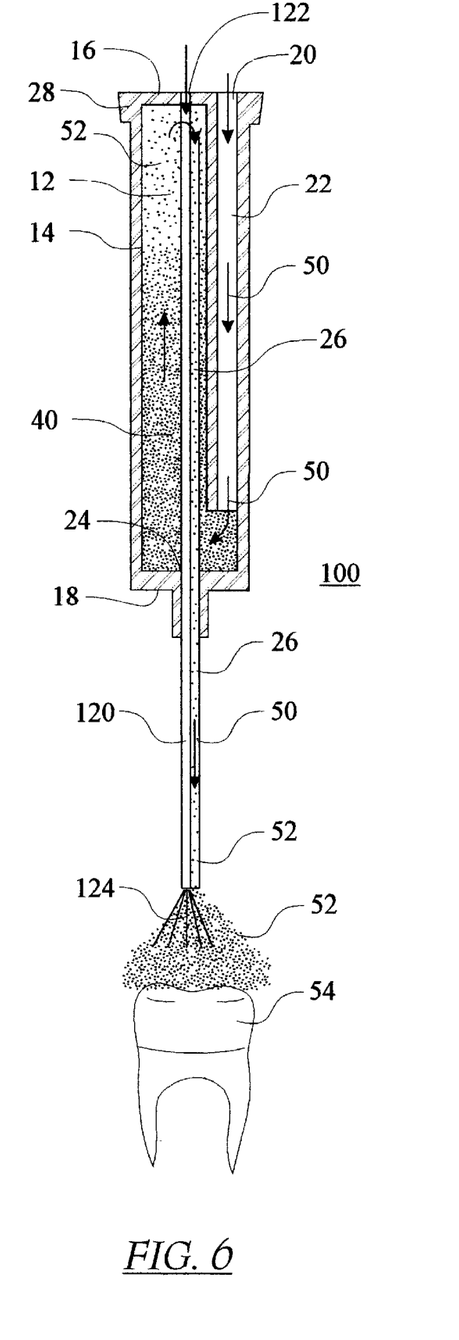
FIG. 6 is a cross sectional view of a multi-conduit particulate matter propelling apparatus wherein an inlet conduit is coupled to the side wall.
Figure 7:
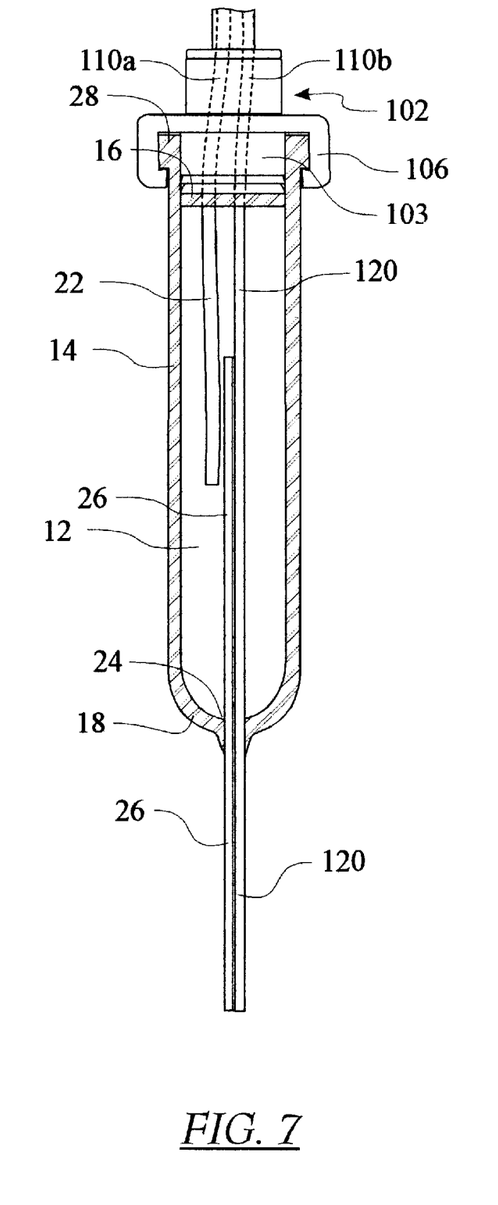
FIG. 7 is a cross sectional view of a multi-conduit particulate matter propelling apparatus wherein the inlet conduits are within the mixing chamber.
Figure 8:
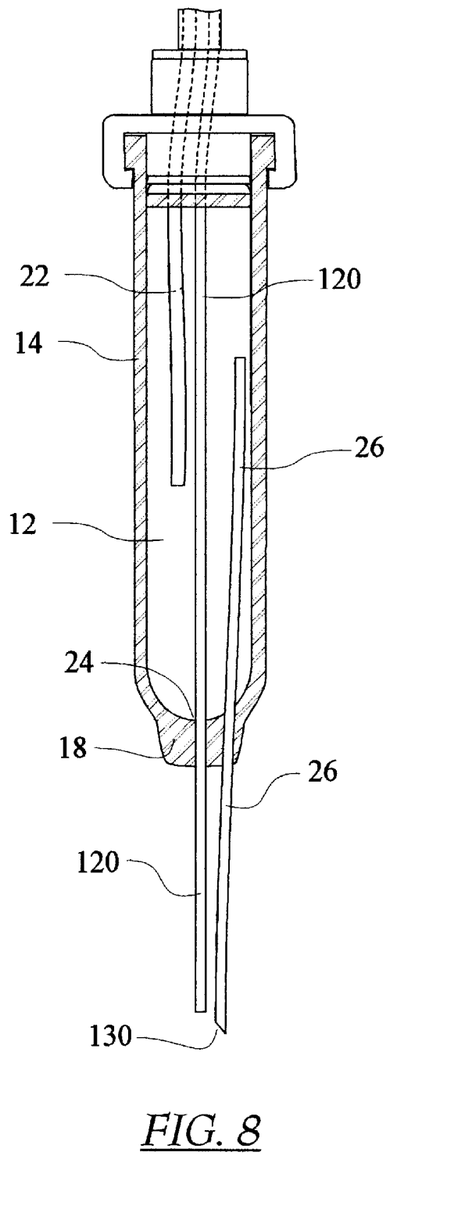
FIG. 8 is a cross sectional view of an alternate multi-conduit particulate matter propelling apparatus.
Figure 9:
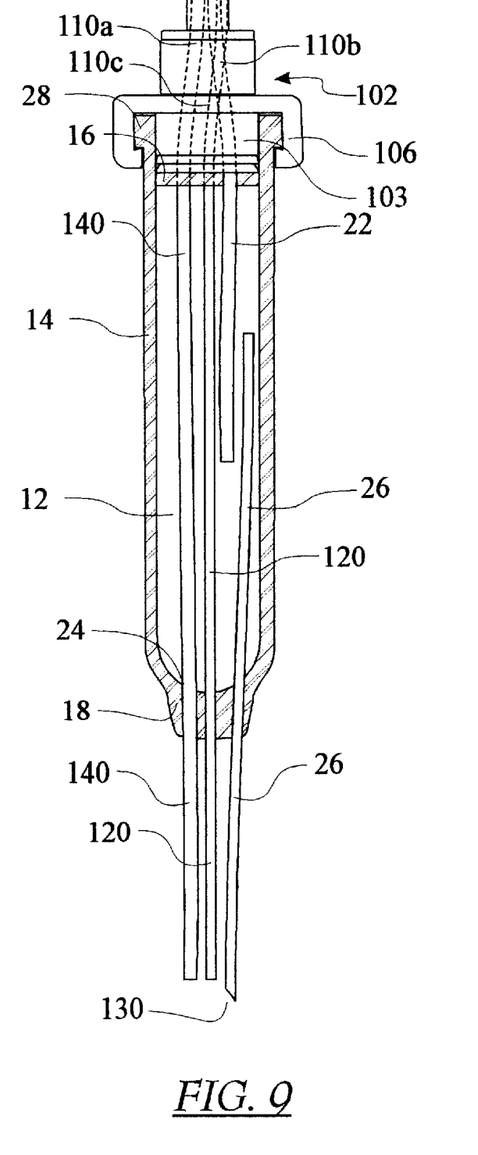
FIG. 9 is a cross sectional view of a second alternate multi-conduit particulate matter propelling apparatus.
Figure 10:
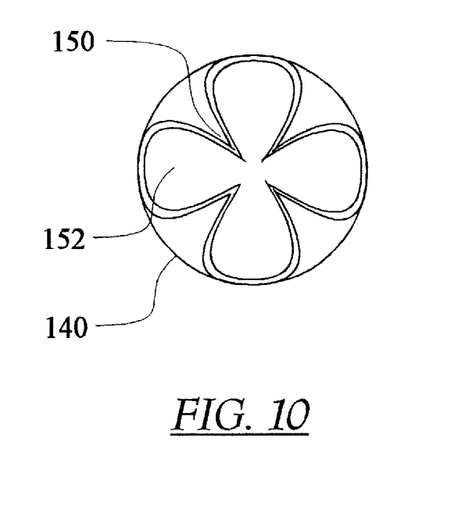
FIG. 10 is an end view of a modified discharge end of a conduit.
Figure 11:
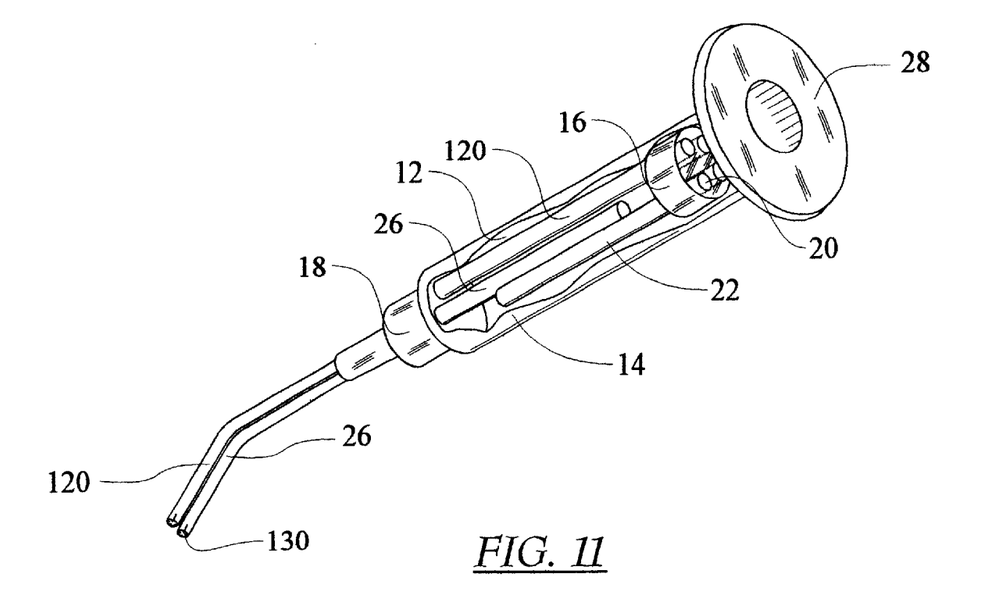
FIG. 11 is a cut-away, isometric view of a multi-conduit particulate matter propelling apparatus.

In practicing the invention, the following method may be used. Various flows are delivered through a multi-conduit connector 102 to a multi-conduit particulate matter propelling apparatus 100. A first port is coupled to a gas receiving port 20 and propellant-gas delivery conduit 22 into mixing chamber 12 through a multi-conduit source supplied by multiple sources (not shown). The gas stream blows through the particulate matter 40 and causes the particulate matter 40 to mix with the gas stream in chamber 12. See FIG. 6. The air and particle mixture 52 enters and passes through discharge conduit 26, and exists apparatus 100 to strike the target material 54, without generating heat, vibration, appreciable noise levels, and having no moving parts. The apparatus 100 provides a means for flow through of other mediums 124 via at least one flow through conduit 120.

In this manner there is provided a disposable apparatus powered by a compressed gas source for propelling particulate matter against a surface of a target material, more particularly against a surface of a dental patient's tooth, within the patient's mouth, as well as a means for passing other mediums (gas, water, and the like) through the apparatus. The apparatus includes a mixing chamber having a chamber wall and a gas receiving port in fluid communication with the compressed gas source, a gas delivery conduit extending from the gas receiving port into the chamber, a mixture discharge conduit extending from the mixture discharge port into the chamber, a quantity of particulate matter inside the chamber, and a flow through conduit in fluid communication with a multi-conduit connector, and exiting the discharge wall 18 of the apparatus 100. The gas is delivered into the propellant-gas delivery conduit 22 and into the mixing chamber 12 from the gas source, the gas stream blows though the quantity of particulate matter 40 and causes the particulate matter to mix with the gas stream in a mixing section on the chamber 12, forming a gas and particle mixture 52 which enters and passes through the discharge conduit 26 and the discharge port (130 of FIG. 8), and exits the apparatus to stake the surface of the target object 54 (shown here as a patient's tooth).

The mixing chamber wall 14 has a tubular side wall portion, a receiving end wall 16 and a discharge end wall 18. The particulate matter 40 does not completely fill said mixing chamber 12. The mixing chamber 12 has a propellant-gas delivery conduit 22 extending into the particulate matter 40, the mixing chamber 12 has a mixture discharge conduit 26 extending into the mixing section of the chamber 12. A discharge conduit 26 as well as the flow through conduit 120 can be of a directing bendable tubes and extend outside and away from the mixing chamber 12. The mixing chamber 12 may be formed of plastic, and may be color-coded to identify the particulate matter 40 contained within the mixing chamber 12. Using this apparatus 100, particulate matter 40 may be propelled against a surface of a target material 54 by delivering a stream of gas into the gas delivery conduit and into the mixing chamber 12 such that the gas stream blows through the particulate matter 40, thereby causing the particulate matter 40 to mix with the gas stream forming a gas/particle mixture 52, and discharging the gas/particulate mixture 52 against a surface of the target 54.

While the invention has been described, disclose illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. Handheld apparatus for propelling particulate matter, the apparatus comprising:

a mixing chamber having a sidewall, a receiving end wall at a one end of the chamber and a discharge end wall at an opposite end of the chamber;

a multi-conduit port in the receiving end wall;

a propellant-gas delivery conduit, whereby the propellant-gas delivery conduit extends in fluid communication from the multi-conduit port towards the discharge end wall;

a discharge port in the discharge end wall;

a discharge conduit wherein a first end of the discharge conduit is in fluid communication within the mixing chamber and a second end can pass material through the discharge end wall; and at least one flow through conduit extending in fluid communication from the multi-conduit port to the discharge end wall.

2. The apparatus of claim 1, wherein the mixing chamber is cylindrical.

3. The apparatus of claim 1, wherein a propellant-gas delivery conduit has one end coupled to the receiving end wall and the opposing end is located internal to the mixing chamber.

4. The apparatus of claim 1, wherein a discharge end of the discharge conduit is externally spaced some distance from the discharge end wall.

5. The apparatus of claim 1, the apparatus further comprising:

a quantity of particulate matter disposed within the mixing chamber and only partially filling the mixing chamber.

6. The apparatus of claim 5, wherein at least one of a portion the apparatus and a volume grid marking is color coded to identify the type of particulate matter disposed within the mixing chamber.

7. The apparatus of claim 1, the apparatus further comprising:

a means for allowing visual observation of the quantity of particulate matter within the mixing chamber.

8. The apparatus of claim 7, wherein the means for allowing visual observation of the quantity of particulate matter within the mixing chamber comprises volume grid markings.

9. The apparatus of claim 1, wherein the mixing chamber is formed of a material selected from the group comprising Delrin™, Polypropolyne™, stainless steel, and disposable plastic.

10. The apparatus of claim 1, wherein the receiving end wall is removable.

11. The apparatus of claim 1, wherein the apparatus sidewall and discharge end wall are constructed from a disposable syringe.

12. The apparatus of claim 1, wherein the at least one conduit has a first cross sectional geometry and the discharge end of the at least one conduit has a second cross sectional geometry, wherein the first cross sectional geometry is different from the second cross sectional geometry.

13. Handheld apparatus for propelling particulate matter, the apparatus comprising:

a mixing chamber having a sidewall, a receiving end wall at a one end of the mixing chamber and a discharge end wall at an opposite end of the mixing chamber;

a multi-conduit port in the receiving end wall;

a propellant-gas delivery conduit, whereby the propellant-gas delivery conduit extends in fluid communication from the multi-conduit port towards the discharge end wall;

a discharge port in the discharge end wall;

a bendable discharge conduit disposed within the mixing chamber and extending in fluid communication from the discharge port towards the receiving end wall;

at least one bendable, flow through conduit extending in fluid communication from the multi-conduit port to the discharge end wall.

14. The apparatus of claim 13, wherein the mixing chamber is cylindrical.

15. The apparatus of claim 13, wherein a propellant-gas delivery conduit has one end coupled to the receiving end wall and the opposing end is located internal to the mixing chamber.

16. The apparatus of claim 13, wherein a discharge end of the discharge conduit is externally spaced some distance from the discharge end wall.

17. The apparatus of claim 13, the apparatus further comprising:

a quantity of particulate matter disposed within the mixing chamber and only partially filling the mixing chamber.

18. The apparatus of claim 17, wherein at least one of a portion the apparatus and a volume grid marking is color coded to identify the type of particulate matter disposed within the mixing chamber.

19. The apparatus of claim 13, the apparatus further comprising:

a means for allowing visual observation of the quantity of particulate matter within the mixing chamber.

20. The apparatus of claim 19, wherein the means for allowing visual observation of the quantity of particulate matter within the mixing chamber comprises volume grid markings.

21. The apparatus of claim 13, wherein the mixing chamber is formed of a material selected from the group comprising Delrin™, Polypropolyne™, stainless steel, and disposable plastic.

22. The apparatus of claim 13, wherein the receiving end wall is removable.

23. The apparatus of claim 13, wherein the apparatus sidewall and discharge end wall are constructed from a disposable syringe.

24. The apparatus of claim 13, wherein the at least one conduit has a first cross sectional geometry and the discharge end of the at least one conduit has a second cross sectional geometry, wherein the first cross sectional geometry is different from the second cross sectional geometry.

* * * * *